United States Patent [19]
Algieri et al.

[11] 4,200,760
[45] Apr. 29, 1980

[54] IMIDAZOLYLALKYLTHIOALKYLAMINO-ETHYLENE DERIVATIVES

[75] Inventors: Aldo A. Algieri, Fayetteville; Ronnie R. Crenshaw, Dewitt, both of N.Y.

[73] Assignee: Bristol-Myers Company, New York, N.Y.

[21] Appl. No.: 945,966

[22] Filed: Sep. 26, 1978

[51] Int. Cl.$^2$ .......................................... C07D 233/64
[52] U.S. Cl. ................................ 548/342; 260/465 E; 260/465.5 R; 260/558 S; 260/561 A; 260/570.5 C; 260/570.5 P; 260/570.5 S; 260/583 EE; 560/16; 560/17; 560/147; 560/153; 424/273 R
[58] Field of Search ......................................... 548/342

[56] References Cited

U.S. PATENT DOCUMENTS

| | | | |
|---|---|---|---|
| 3,932,443 | 1/1976 | White | 548/342 |
| 3,953,460 | 4/1976 | Durant et al. | 548/342 |
| 3,968,227 | 7/1976 | Durant et al. | 424/273 R |
| 4,013,678 | 3/1977 | Brown et al. | 548/342 |
| 4,028,379 | 6/1977 | White | 548/342 |
| 4,049,671 | 9/1977 | Durant et al. | 548/342 |
| 4,098,898 | 7/1978 | Durant et al. | 548/342 |
| 4,112,234 | 9/1978 | Crenshaw et al. | 548/342 |

FOREIGN PATENT DOCUMENTS

| | | | |
|---|---|---|---|
| 843840 | 1/1977 | Belgium | 548/342 |
| 857388 | 2/1978 | Belgium | 548/342 |

OTHER PUBLICATIONS

Drugs of the Future 1976, vol. 1, No. 1, pp. 13–18.
Ganellin et al., Federation Proceedings 1976, vol. 35, pp. 1924–1930.

*Primary Examiner*—Natalie Trousof
*Attorney, Agent, or Firm*—Richard R. Lloyd

[57] ABSTRACT

Compounds of the formula

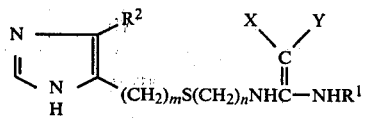

wherein $R^1$ is a straight or branched chain alkynyl group containing from 3 to 9 carbon atoms, inclusive; $R^2$ is hydrogen, (lower)alkyl, halogen or hydroxymethyl; m is 1 or 2, and n is 2 or 3, provided that the sum of m and n is 3 or 4; X and Y each are independently hydrogen, nitro, cyano, —SO$_2$Ar or —COR$^3$, provided that X and Y are not both hydrogen; $R^3$ is (lower)alkyl, Ar, (lower)alkoxy, amino or (lower)-alkylamino; and Ar is an optionally substituted phenyl group; and nontoxic pharmaceutically acceptable acid addition salts thereof, are potent anti-ulcer agents. Processes for their preparation and novel intermediates are also disclosed.

14 Claims, No Drawings

IMIDAZOLYLALKYLTHIOALKYLAMINO-ETHYLENE DERIVATIVES

SUMMARY OF THE INVENTION

This application relates to certain 1-alkynylamino-1-{ω-[(4-optionally substituted-1H-imidazol-5-yl)alkylthio]alkylamino}ethylene derivatives which are $H_2$-receptor blocking agents, which inhibit gastric acid secretion and which are useful in the treatment of ulcers, and to processes for their preparation.

BACKGROUND AND PRIOR ART

The clinical objective in treatment of peptic ulcer disease is to decrease gastric acid secretion, based on the principle "no acid, no ulcer." Traditional peptic ulcer disease therapy involves control of diet and the use of antacids and anticholinergics.

There is evidence indicating that histamine may be the final common pathway for stimulation of gastric secretion. This effect of histamine is mediated via $H_2$ receptors and is not inhibited by the classical antihistamines, which are $H_1$-receptor blockers. A number of specific $H_2$-receptor blocking agents ($H_2$-receptor antagonists) are now known. These compounds inhibit basal acid secretion, as well as secretion by other known gastric acid stimulants, and are useful in the treatment of peptic ulcers.

Burimamide (IIa) was the first clinically effective $H_2$-receptor antagonist. It inhibits gastric secretion in animals and man, but oral absorption is poor.

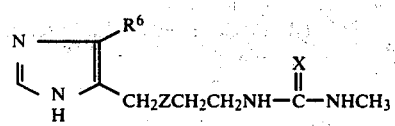

II

IIa; $R^6$=H, Z=$CH_2$, X=S Burimamide
b; $R^6$=$CH_3$, Z=S, X=S Metiamide
c; $R^6$=$CH_3$, Z=S, X=NCN Cimetidine Metiamide (IIb), a subsequently evaluated $H_2$ antagonist, is more potent than burimamide and is orally active in man. Clinical utility was limited, however, owing to toxicity (agranulocytosis). Cimetidine (IIc) is as effective an $H_2$ antagonist as metiamide, without producing agranulocytosis, and has recently been marketed as an anti-ulcer drug. The half-life of cimetidine is relatively short, thereby necessitating a therapeutic regimen of multi daily doses of 200-300 mg. tablets. There is thus a need for anti-ulcer agents which are longer acting and/or more potent than cimetidine.

Reviews on the development of $H_2$ antagonists, including those discussed in the preceding paragraph, may be found in C. R. Ganellin, et al., *Federation Proceedings*, 35, 1924 (1976), in *Drugs of the Future*, 1, 13 (1976), and in references cited therein. Relevant patents are as follows:

Belgian Pat. No. 841,814 (Farmdoc 90568X) discloses inhibitors of histamine-stimulated gastric secretion having the formula

in which HET is one of eight named heterocyclic rings (including imidazole) which may be substituted by (lower)alkyl, hydroxyl, amino or halogen, Z is sulfur or $CH_2$, X is S, $CHNO_2$, NCN or NH, Y is $NH_2$, (lower)alkylamino, di(lower)alkylamino, (lower)alkoxy, phenylethyl, imidazolylethyl, allyl, trifluoroethyl or $(CH_2)_nR$ in which n is 1-12 and R is OH, (lower)alkoxy, $NH_2$ or (lower)alkylamino; provided that, when X is NH, Y is trifluoroethyl or $(CH_2)_nR$; and when X is NCN, Y may not be amino or alkylamino.

U.S. Pat. No. 4,112,234 discloses histamine $H_2$-receptor inhibitors of the formula

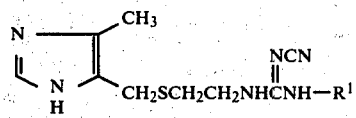

wherein $R^1$ is a straight or branched chain alkynyl group containing from 3 to 9 carbon atoms, and processes for the preparation thereof.

Belgian Pat. No. 843,840 (Farmdoc 05613Y) discloses histamine $H_2$-receptor antagonists having the formula

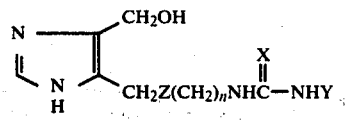

wherein n is 2-3, Z is sulfur or $CH_2$, Y is inter alia lower alkyl, and X is sulfur, $CHNO_2$ or NCN.

U.K. Pat. No. 1,421,792 discloses $H_2$-receptor inhibitors of the formula

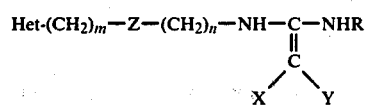

wherein X and Y, which may be the same or different, are hydrogen, nitro, cyano or $SO_2Ar$, but may not both be hydrogen; R is hydrogen, (lower)alkyl or Het$(CH_2)_mZ(CH_2)_n$; Z is sulfur or methylene; m is 0, 1 or 2 and n is 2 or 3 provided that the sum of m and n is 3 or 4; Het is an imidazole, pyridine, thiazole, isothiazole, oxazole, isoxazole, triazole or thiadiazole ring which is optionally substituted by (lower)alkyl, hydroxy, halogen or amino; and Ar is phenyl, optionally substituted by halogen, methyl or amino.

Belgian Pat. No. 814,941 (Farmdoc 82621V) is substantially identical to U.K. Pat. No. 1,421,792, differing primarily in that the broadest definition of Het is a 5- or 6-membered nitrogen-containing ring, and that the definition of Ar is an aryl group optionally substituted by halogen, methyl or amino.

Farmdoc indicates the following U.S. patents to be concordant with Belgian Pat. No. 814,941: U.S. Pat. Nos. 3,953,460, 4,002,759, 4,013,769, 4,024,260, 4,046,907, 4,067,984 and 4,080,459. Each of these U.S. patents discloses as a preferred embodiment a portion of Belgian Pat. No. 841,941 and U.K. Pat. No. 1,421,792.

Belgian Pat. No. 857,388 discloses histamine $H_2$-receptor inhibitors of the formula

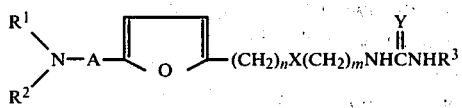

in which $R^1$ and $R^2$ are the same or different and are hydrogen, (lower)alkyl, cycloalkyl, (lower)alkenyl, aralkyl or a (lower)alkyl group which is interrupted by an oxygen atom or by the group $NR^4$ in which $R^4$ is hydrogen or (lower)alkyl, or $R^1$ and $R^2$ together with the nitrogen atom form a heterocyclic ring optionally containing an oxygen atom or an $NR^4$ group; A is (lower)alkylene; m is 2–4; n is 1 or 2, or can be zero when X is sulfur or $CH_2$; X is oxygen, sulfur or $CH_2$; Y is sulfur, oxygen, $NR^5$ or $CHR^6$; $R^5$ is hydrogen, nitro, cyano, (lower)alkyl, aryl, alkylsulfonyl or arylsulfonyl; $R^6$ is nitro, arylsulfonyl or alkylsulfonyl; and $R^3$ is hydrogen, (lower)alkyl, (lower)alkenyl or alkoxyalkyl. This patent also discloses compounds of the formula

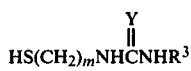

wherein m and $R^3$ are as defined above, as intermediates in the preparation of the above $H_2$-receptor inhibitors.

U.S. Pat. No. 4,028,379 discloses intermediates (and a process for their preparation) which are useful in the preparation of histamine $H_2$ antagonists, said intermediates having the formula

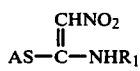

wherein A is (lower)alkyl and $R_1$ is (lower)alkyl, (lower)alkoxy, 2,2,2-trifluoroethyl, $(CH_2)_nR_2$ or $HetCH_2Z(CH_2)_2$; in which Het is an imidazole, thiazole, pyridine, isothiazole, oxazole, isoxazole, triazole or thiadiazole ring which is optionally substituted by (lower)alkyl, hydroxyl, (lower)alkoxy, chlorine or bromine; Z is sulfur or methylene; n is an integer of from 1 to 12; and $R_2$ is hydroxy, (lower)alkoxy or (lower)alkylamino. The patent also discloses the use of these intermediates for the preparation of $H_2$ antagonists of the formula

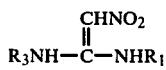

in which $R_3$ is (lower)alkyl, (lower)alkoxy, 2,2,2-trifluoroethyl, $(CH_2)_nR_2$ or $HetCH_2Z(CH_2)_2$, provided that, if $R_1$ is not $HetCH_2Z(CH_2)_2$, then $R_3$ must be $HetCH_2Z(CH_2)_2$.

COMPLETE DISCLOSURE

This invention relates to histamine $H_2$-receptor antagonists which are effective inhibitors of gastric secretion in animals, including man, which are useful in the treatment of peptic ulcer disease, and which have the formula

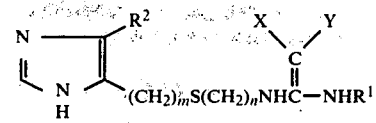

wherein $R^1$ is a straight or branched chain alkynyl group containing from 3 to 9 carbon atoms, inclusive; $R^2$ is hydrogen, (lower)alkyl, halogen, or hydroxymethyl; m is 1 or 2, and n is 2 or 3, provided that the sum of m and n is 3 or 4; X and Y each are independently hydrogen, nitro, cyano, $-SO_2Ar$ or $-COR^3$, provided that X and Y are not both hydrogen; $R^3$ is (lower)alkyl, Ar, (lower)alkoxy, amino or (lower)alkylamino; and Ar is phenyl or phenyl containing 1 or 2 substituents independently selected from halogen and (lower)alkyl; and nontoxic pharmaceutically acceptable acid addition salts thereof.

A preferred embodiment of the invention is a compound of the formula

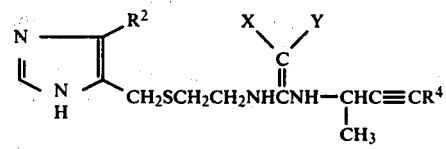

wherein $R^2$, X and Y are as defined above, and $R^4$ is hydrogen or methyl, or a nontoxic pharmaceutically acceptable acid addition salt thereof.

Another preferred embodiment of the invention is a compound of the formula

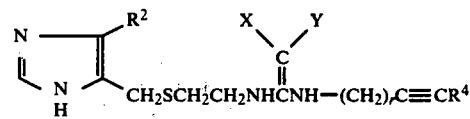

wherein $R^2$, X and Y are as defined above, $R^4$ is hydrogen or methyl and r is an integer of from 1 to 6, inclusive, or a nontoxic pharmaceutically acceptable acid addition salt thereof.

Another preferred embodiment of the invention is a compound of the formula

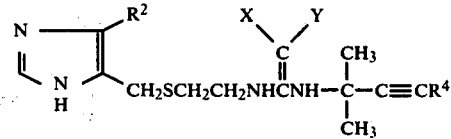

wherein $R^2$, X and Y are as defined above, and $R^4$ is hydrogen or methyl, or a nontoxic pharmaceutically acceptable acid addition salt thereof.

A more preferred embodiment of the invention is a compound of the formula

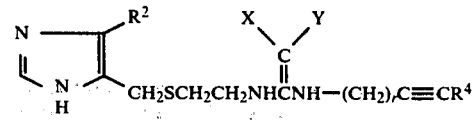

wherein R² is methyl, chloro, bromo or hydroxymethyl; X and Y are each independently hydrogen, nitro, cyano or carbamoyl, provided that X and Y are not both hydrogen; r is an integer of from 1 to 6; and R⁴ is hydrogen or methyl; or a nontoxic, pharmaceutically acceptable salt thereof.

Another more preferred embodiment of the invention is 1-carbamoyl-1-cyano-2-(2-propynylamino)-2-{2-[(4-methyl-1H-imidazol-5-yl)methylthio]ethylamino}ethylene or a nontoxic pharmaceutically acceptable salt thereof.

Another more preferred embodiment of the invention is 1,1-dicyano-2-(2-propynylamino)-2-{2-[(4-methyl-1H-imidazol-5-yl)methylthio]ethylamino}ethylene or a nontoxic pharmaceutically acceptable salt thereof.

Another more preferred embodiment of the invention is 1-nitro-2-(2-methyl-3-butyn-2-ylamino)-2-{2-[(4-methyl-1H-imidazol-5-yl)methylthio]ethylamino}ethylene or a nontoxic pharmaceutically acceptable salt thereof.

Another more preferred embodiment of the invention is 1-nitro-2-(3-butyn-1-ylamino)-2-{2-[(4-methyl-1H-imidazol-5-yl)methylthio]ethylamino}ethylene or a nontoxic pharmaceutically acceptable salt thereof.

Another more preferred embodiment of the invention is 1-nitro-2-(3-butyn-2-ylamino)-2-{2-[(4-methyl-1H-imidazol-5-yl)methylthio]ethylamino}ethylene or a nontoxic pharmaceutically acceptable salt thereof.

Another more preferred embodiment of the invention is 1-nitro-2-(4-pentyn-1-ylamino)-2-{2-[(4-methyl-1H-imidazol-5-yl)methylthio]ethylamino}ethylene or a nontoxic pharmaceutically acceptable salt thereof.

Another more preferred embodiment of the invention is 1-nitro-2-(2-butyn-1-ylamino)-2-{2-[(4-methyl-1H-imidazol-5-yl)methylthio]ethylamino}ethylene or a nontoxic pharmaceutically acceptable salt thereof.

The most preferred embodiment of the invention is 1-nitro-2-(2-propynylamino)-2-{2-[(4-methyl-1H-imidazol-5-yl)methylthio]ethylamino}ethylene or a nontoxic pharmaceutically acceptable salt thereof.

Although the compounds of this invention have been shown as having the structure of Formula I, it will be appreciated by those skilled in the art that the compounds can exist in various tautomeric forms, as follows:

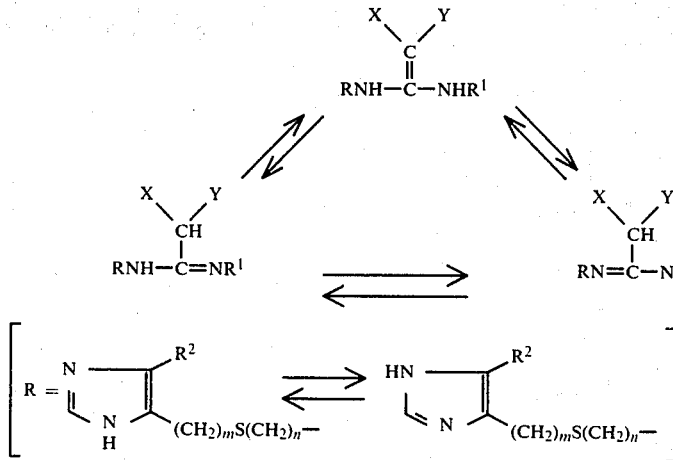

Accordingly, it should be understood that the compounds of Formula I may be named as 1-alkynyl-1-{2-[(5-optionally substituted-1H-imidazol-4-yl)alkylthio)ethylenes as well as the names utilized herein. Also, when X and Y are different, the compounds of this invention may exist as two geometric isomers, i.e. cis-/trans isomers about the double bond. In addition, the compounds of Formula I which contain a branched chain alkynyl group as substituent R¹ may exist as their d- or l- optical isomers as well as their racemic forms. Thus, for example 3-amino-1-butyne of the formula

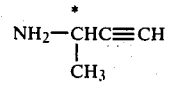

may be resolved into its d- and l- isomers as described by A. Marszak-Fleury, *Compt. rend.*, 242, 1046 (1956). The use of the d- or l- isomer of the alkynylamine in the preparation of a compound of Formula I produces the corresponding d- or l- isomer of the compound of Formula I. The present invention includes within its scope all possible tautomeric forms, geometric isomers and optical isomers of the compounds of Formula I as well as mixtures thereof.

The compounds of the present invention may be prepared by alternative reaction schemes, as illustrated below for the most preferred compound Ia.

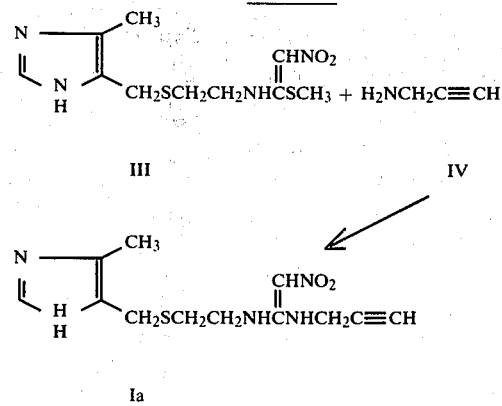

Reaction scheme I is conducted in a non-reactive solvent system at or above room temperature. Although reaction scheme I is illustrated with a methylthio group as the leaving group, any conventional leaving group may be utilized in the reaction, e.g. (lower)alkylthio, arylthio, substituted arylthio such as p-nitrophenylthio, aralkylthio, cyanomethylthio, carboxymethylthio or an ester thereof, or the like. Preferred leaving groups are (lower)alkylthio (and particularly methylthio), phenyl(-lower)alkkylthio and phenylthio containing 1 or 2 substituent groups independently selected from nitro, chloro and bromo. The compound of Formula III is prepared as described in U.S. Pat. No. 4,046,907, and analogous starting materials may be prepared by analogous procedures. The alkynylamines such as compound IV are commercially available or may be prepared by methods described in Bull. Soc. Chim. Fr., 490 (1958), Bull. Soc. Chim. Fr., 588 (1967), Bull. Soc. Chim. Fr. 592 (1967), Annals de Chimie (Paris), 3, 656 (1958) and J. Org. Chem., 21, 791 (1956).

preferable for the preparation of some of the compounds of Formula I. The preparation of compound Ia is illustrated.

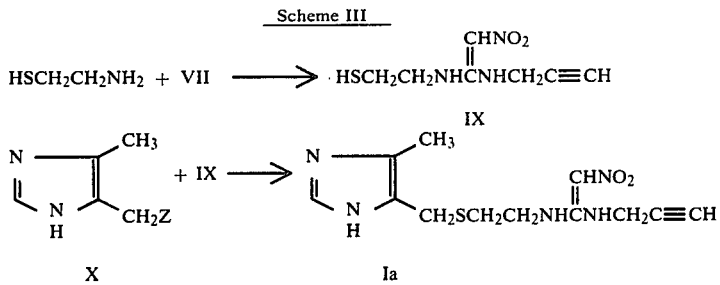

In reaction scheme III compound X preferably is used in the form of an acid addition salt thereof. The reaction is conducted in a non-reactive organic solvent and preferably in the presence of a base. Substituent Z is a conventional leaving group. Suitable leaving groups "Z" for use in this reaction are well-known to those skilled in the art. They include, for example, fluoro, chloro, bromo, iodo, $-O_3SR^7$ wherein $R^7$ is (lower)alkyl [e.g. methanesulfonate], $-O_3SR^8$ wherein $R^8$ is aryl or substituted aryl [e.g. benzenesulfonate, p-bromobenzenesulfonate or p-toluenesulfonate], $-O_3SF$, acetoxy and 2,4-dinitrophenoxy. For convenience and economy we normally prefer to utilize compound X in which Z is chloro. Alternatively, Z may be the hydroxyl group

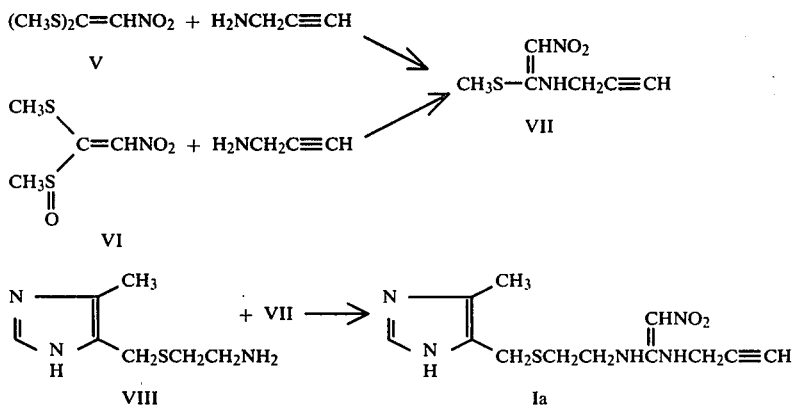

Reaction scheme II is conducted in a non-reactive solvent at or above room temperature. In compound VII the leaving group is shown as the methylthio group but any conventional leaving group may be utilized, e.g. as disclosed above for reaction scheme I. Preferred leaving groups are (lower)alkyl (and particularly methylthio), phenyl(lower)alkylthio and phenylthio containing 1 or 2 substituents independently selected from nitro, chloro and bromo. The compound of Formula V may be prepared by procedures described by Gompper and Schaefer, Chem. Ber., 100, 591 (1967) and Buchardt and Lohse, Acta Chem. Scand., 21, 2797 (1967). The compound of Formula VI may be prepared by the procedure described in Belgian Pat. No. 841,526. The compound of Formula VIII may be prepared by the procedures described in U.S. Pat. Nos. 3,950,353 and 4,049,672, and analogous compounds may be prepared by analogous procedures.

Other synthetic schemes for the preparation of the compounds of Formula I are envisioned and may be when the reaction is conducted in the presence of a strong acid such as hydrochloric acid.

Scheme IV

[Structure VIII: imidazole with CH3 and CH2SCH2CH2NH2 substituents] + CH3SCNHCH2C≡CH with CHNO2 group (XI)
                                                        ‖
                                                        O

↓

[Structure Ia: imidazole with CH3 and CH2SCH2CH2NHCNHCH2C≡CH with CHNO2 group]

Compound XI may be prepared by oxidation of compound VII by methods well-known in the art. The reaction is conducted in a non-reactive solvent at or above room temperature. Although reaction scheme IV is illustrated with a methylsulfinyl group as the leaving group in compound XI, the methylsulfinyl group may be replaced by (lower)alkylsulfinyl, arylsulfinyl, substituted arylsulfinyl such as p-nitrophenylsulfinyl, aralkylsulfinyl, cyanomethylsulfinyl, carboxymethylsulfinyl or an ester thereof, or the like.

Another aspect of this invention relates to intermediates of the formula $$\begin{array}{c} X\diagdown \diagup Y \\ C \\ \| \\ HS(CH_2)_nNHCNH-R^1 \end{array}$$ XIII wherein $R^1$, X, Y and n are as defined above, which are useful in preparing the histamine $H_2$-receptor antagonists of Formula I.

In a preferred embodiment, $R^1$ of the intermediate of Formula XIII is $$-CHC\equiv CR^4$$
$$\phantom{-}|\phantom{HC\equiv CR^4}$$
$$\phantom{-}CH_3$$

in which $R^4$ is hydrogen or methyl; in another preferred embodiment of intermediate XIII $R^1$ is $-(CH_2)_rC\equiv CR^4$ in which r is an integer of from 1 to 6 and $R^4$ is hydrogen or methyl; in another preferred embodiment of intermediate XIII $R^1$ is $$\phantom{-}CH_3$$
$$\phantom{-}|$$
$$-C-C\equiv CR^4$$
$$\phantom{-}|$$
$$\phantom{-}CH_3$$

in which $R^4$ is hydrogen or methyl.

In another preferred embodiment, intermediate XIII has the structure XIIIa $$\begin{array}{c} X\diagdown \diagup Y \\ C \\ \| \\ HSCH_2CH_2NHCNH-(CH_2)_rC\equiv R^4 \end{array}$$ XIIIa wherein $R^4$ is hydrogen or methyl, r is an integer of from 1 to 6; and X and Y are each independently hydrogen, nitro, cyano or carbamoyl, provided that X and Y are not both hydrogen.

A more preferred embodiment of the intermediate of Formula XIII is 1-(2-propyn-1-yl)amino-1-(2-mercaptoethyl)amino-2-carbamoyl-2-cyanoethylene.

Another more preferred embodiment of the intermediate of Formula XIII is 1-(2-propyn-1-yl)amino-1-(2-mercaptoethyl)amino-2,2-dicyanoethylene.

Another more preferred embodiment of the intermediate of Formula XIII is 1-(4-pentyn-1-yl)amino-1-(2-mercaptoethyl)amino-2-nitroethylene.

Another more preferred embodiment of the intermediate of Formula XIII is 1-(2-butyn-1-yl)amino-1-(2-mercaptoethyl)amino-2-nitroethylene.

Another more preferred embodiment of the intermediate of Formula XIII is 1-(2-methyl-3-butyn-2-yl)amino-1-(2-mercaptoethyl)amino-2-nitroethylene.

Another more preferred embodiment of the intermediate of Formula XIII is 1-(3-butyn-1-yl)amino-1-(2-mercaptoethyl)amino-2-nitroethylene.

Another more preferred embodiment of the intermediate of Formula XIII is 1-(3-butyn-2-yl)amino-1-(2-mercaptoethyl)amino-2-nitroethylene.

The most preferred embodiment of the intermediate of Formula XIII is 1-(2-propyn-1-yl)amino-1-(2-mercaptoethyl)amino-2-nitroethylene.

The intermediates of Formula XIII may be prepared by the reaction of a mercaptoalkylamine of the formula $$HS(CH_2)_nNH_2$$ XIV wherein n is as defined above, with a compound of the formula $$\begin{array}{c} X\diagdown \diagup Y \\ C \\ \| \\ R^5S-CNH-R^1 \end{array}$$ XV where $R^1$, X and Y are as defined above and $R^5$ is (lower) alkyl, phenylalkyl or phenyl containing 1 or 2 substituents independently selected from nitro, chloro and bromo.

The intermediates of Formula XIII may also be prepared by the reaction of a compound of Formula XV with a protected mercaptoalkylamine of Formula XIVa $$P-S(CH_2)_nNH_2$$ XIVa wherein n is as described above and P is any of the suitable sulfhydryl protecting groups known in the art, followed by removal of the sulfhydryl protecting group.

The compound of Formula XIV or XIVa preferably is used in the form of an acid addition salt (most preferably its hydrochloride) and is reacted with about an equimolar amount of a compound of Formula XV in a non-reactive solvent such as ethanol, isopropanol or dimethylformamide. An equimolar amount of a base such as sodium hydroxide is added. The reaction may be conducted at or above room temperature. At the conclusion of the reaction the reaction mixture is evaporated to dryness and the desired product of Formula XIII is extracted from the by-product salt with a solvent such as ethanol. When an alcohol such as ethanol is utilized as solvent, one may simply separate the insoluble salts from the reaction mixture by filtration.

It is desirable to conduct the reaction of Compounds XIV and XV in the presence of a small amount of hydroquinone and to bubble nitrogen through the reaction mixture. These conditions produce compounds of Formula XIII in higher yield and of higher purity. The nitrogen sweep is believed to remove the mercaptan produced in the reaction (methyl mercaptan when $R^5$ is the preferred methyl group) and thereby avoid secondary reactions arising from the addition of the mercaptan to the carbon-carbon triple bond. It is believed that the hydroquinone prevents the formation of free radicals and secondary reactions arising from their presence.

Starting material XIV in which n is 2, cysteamine, is commercially available. Compound XIV in which n is 3, 3-mercaptopropylamine, may be prepared by the procedure described by S. D. Turk, et al. in *J. Org. Chem.*, 27, 2846 (1962).

A compound of Formula XIII may be reacted with a compound of Formula XVI

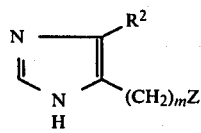   XVI wherein $R^2$, m and Z are as defined above, to produce an anti-ulcer compound of Formula I. The reaction may be conducted in a non-reactive solvent such as a (lower)alkanol, acetonitrile, dimethylformamide, dimethylsulfoxide, or the like. We prefer to utilize ethanol as the solvent. Leaving group "Z" of Compound XVI preferably is chloro and Compound XVI is preferably in the form of an acid addition salt (e.g. the hydrochloride). Approximately equimolar amounts of the two reactants are utilized and the reaction preferably is conducted in the presence of at least an equimolar amount of a base such as sodium hydroxide. The reaction may be conducted at or above room temperature. The reaction mixture is filtered through celite, evaporated to dryness and the desired product is purified by chromatography on silica gel as described for related compounds in our colleagues U.S. Pat. No. 4,112,234, the disclosure of which is incorporated herein by reference.

Still another aspect of this invention relates to intermediates of Formula XV

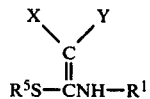   XV in which $R^1$, X, Y and $R^5$ are as defined above.

In a preferred embodiment, $R^1$ of intermediate XV is

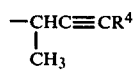

in which $R^4$ is hydrogen or methyl; in another preferred embodiment of intermediate XV, $R^1$ is —$(CH_2)_rC\equiv CR^4$ in which r is an integer of from 1 to 6 and $R^4$ is hydrogen or methyl; in another preferred embodiment of intermediate XV, $R^1$ is

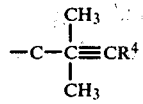

in which $R^4$ is hydrogen or methyl.

In another preferred embodiment intermediate XV has the structure XVa

   XVa in which $R^4$ is hydrogen or methyl; r is an integer of from 1 to 6; X and Y are each independently selected from hydrogen, nitro, cyano or carbamoyl, provided that X and Y are not both hydrogen; and $R^5$ is (lower)alkyl.

A more preferred embodiment of intermediate XV is 1-(2-propyn-1-yl)amino-1-methylthio-2-carbamoyl-2-cyanoethylene.

Another more preferred embodiment of intermediate XV is 1-(2-propyn-1-yl)amino-1-methylthio-2,2-dicyanoethylene.

Another more preferred embodiment of intermediate XV is 1-(4-pentyn-1-yl)amino-1-methylthio-2-nitroethylene.

Another more preferred embodiment of intermediate XV is 1-(3-butyn-2-yl)amino-1-methylthio-2-nitroethylene.

Another more preferred embodiment of intermediate XV is 1-(2-butyn-1-yl)amino-1-methylthio-2-nitroethylene.

Another more preferred embodiment of intermediate XV is 1-(3-butyn-1-yl)amino-1-methylthio-2-nitroethylene.

Another more preferred embodiment of intermediate XV is 1-(2-methyl-3-butyn-2-yl)amino-1-methylthio-2-nitroethylene.

The most preferred embodiment of intermediate XV is 1-(2-propyn-1-yl)amino-1-methylthio-2-nitroethylene.

An intermediate of Formula XV may be reacted with a compound of Formula XIV to produce an intermediate of Formula XIII which may, in turn, be reacted with a compound of the formula

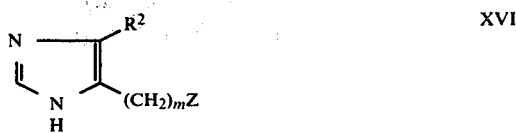   XVI wherein $R^2$, m and Z are as defined above, to produce an anti-ulcer compound of Formula I. This is the procedure outlined in reaction Scheme III. Alternatively, intermediate XV may be reacted directly with a compound of the formula

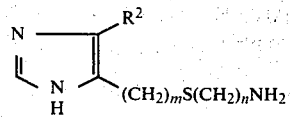

wherein R², m and n are as defined above, to produce an anti-ulcer compound of Formula I. This is the procedure outlined in reaction Scheme II.

As used herein, the term nontoxic pharmaceutically acceptable acid addition salt means the mono- or di-salt of a compound of this invention with a nontoxic pharmaceutically acceptable organic or inorganic acid. Such acids are well known and include hydrochloric, hydrobromic, sulfuric, sulfamic, phosphoric, nitric, maleic, fumaric succinic, oxalic, benzoic, methanesulfonic, ethanedisulfonic, benzenesulfonic, acetic, propionic, tartaric, citric, camphorsulfonic, and the like. The salts are made by methods known in the art.

As used herein and in the claims the term "(lower)alkyl" means a straight or branched chain alkyl group containing from 1 to 6 carbon atoms.

For therapeutic use, the pharmacologically active compounds of this invention will normally be administered as a pharmaceutical composition comprising as the (or an) essential active ingredient at least one such compound in the basic form or in the form of a nontoxic pharmaceutically acceptable acid addition salt, in association with a pharmaceutically acceptable carrier.

The pharmaceutical compositions may be administered orally, parenterally or by rectal suppository. A wide variety of pharmaceutical forms may be employed. Thus, if a solid carrier is used, the preparation may be tableted, placed in a hard gelatin capsule in powder or pellet form, or in the form of a troche or lozenge. If a liquid carrier is employed, the preparation may be in the form of a syrup, emulsion, soft gelatin capsule, sterile solution for injection, or an aqueous or nonaqueous liquid suspension. The pharmaceutical compositions are prepared by conventional techniques appropriate to the desired preparation.

Preferably, each dosage unit will contain the active ingredient in an amount of from about 50 mg. to about 250 mg., and most preferably from about 100 mg. to about 200 mg.. The active ingredient will preferably be administered in equal doses from two to four times a day. The daily dosage regimen will preferably be from 250 mg. to about 1000 mg., and most preferably from about 500 mg. to about 750 mg.

Histamine H₂-receptor antagonists have been shown to be effective inhibitors of gastric secretion in animals and man, Brimblecombe et al., J. Int. Med. Res., 3, 86 (1975). Clinical evaluation of the histamine H₂-receptor antagonist cimetidine has shown it to be an effective therapeutic agent in the treatment of peptic ulcer disease, Gray et al., Lancet, 1 (8001), 4 (1977). The compound prepared in Example 1 below (hereinafter referred to as BL-5949) has been compared with cimetidine and with the structurally related compound of Formula XII

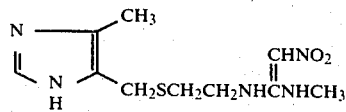

(disclosed in Belgian Pat. No. 814,941) in various tests, and has been shown to be more potent than either cimetidine or Compound XII both as a histamine H₂-receptor antagonist in isolated guinea pig atria and as an inhibitor of gastric secretion in rats and dogs.

Histamine and H₂-Receptor Antagonism-Isolated Guinea Pig Atria Assay

Histamine produces concentration-related increases in the contractile rate of isolated, spontaneously beating guinea pig right atria. Black et al., Nature, 236, 385 (1972), described the receptors involved in this effect of histamine as histamine H₂-receptors when they reported the properties of burimamide, a competitive antagonist of these receptors. Subsequent investigations by Hughes and Coret, Proc. Soc. Exp. Biol. Med., 148, 127 (1975) and Verma and McNeill, J. Pharmacol. Exp. Ther., 200, 352 (1977) support the conclusion of Black and coworkers that the positive chronotropic effect of histamine in isolated guinea pig right atria is mediated via histamine H₂-receptors. Black et al., Agents and Actions, 3, 133 (1973) and Brimblecombe et al., Fed. Proc., 35, 1931 (1976) have utilized isolated guinea pig right atria as a means for comparing the activities of histamine H₂-receptor antagonists. The present comparative studies were carried out using a modification of the procedure reported by Reinhardt et al., Agents and Actions, 4, 217 (1974).

Male Hartley strain guinea pigs (350–450 gm.) were sacrificed by a blow on the head. The heart was excised and placed in a Petri dish of oxygenated (95% $O_2$, 5% $CO_2$) modified Krebs solution (g./liter: NaCl 6.6, KCl 0.35, $MgSO_4.7 H_2O$ 0.295, $KH_2PO_4$ 0.162, $CaCl_2$ 0.238, $NaHCO_3$ 2.1 and dextrose 2.09). The spontaneously beating right atrium was dissected free from other tissues and a silk thread (4-O) attached to each end. The atrium was suspended in a 20 ml. muscle chamber containing oxygenated modified Krebs solution maintained at 32° C. Atrial contractions were recorded isometrically by means of a Grass FT 0.03 force displacement transducer and recordings of contractile force and rate were made with a Beckman RP Dynograph.

A resting tension of 1 g. was applied to the atrium and it was allowed to equilibrate for 1 hour. At the end of the equilibration period a submaximal concentration of histamine dihydrochloride ($3 \times 10^{-6}$ M) was added to the bath and washed out to prime the tissue. Histamine was then added to the bath in a cumulative fashion using ½ log 10 intervals to give final molar bath concentrations of $1 \times 10^{-7}$ to $3 \times 10^{-5}$. The histamine-induced increase in atrial rate was allowed to plateau before the next successive concentration was added. The maximal response invariably occurred at the $3 \times 10^{-5}$ M concentration. The histamine was washed out several times and the atrium allowed to return to control rate. The test compound ($3 \times 10^{-5}$ M) was then added and after a 30 minute incubation the histamine concentration-response was repeated adding higher concentrations as needed.

The histamine ED50 values (concentration of histamine which increased contractile rate 50% of maximum) and 95% confidence limits before and after the test compound were obtained by regression analysis as described by Finney, Probit Analysis, 3rd ed., Cambridge (1971). Concentration-response curve displacement factors were calculated as follows:

$$\text{Displacement Factor} = \frac{\text{ED50 Histamine + Compound}}{\text{ED50 Histamine Alone}}$$

The factors obtained for BL-5949 and Compound XII were then expressed as ratios of the factor obtained for cimetidine.

$$\text{Activity Ratio} = \frac{\text{Test Compound Displacement Factor} - 1}{\text{Cimetidine Displacement Factor} - 1}$$

The results obtained from these studies are summarized in Table 1. Cimetidine, Compound XII and BL-5949 displaced the histamine concentration-response curve to the right by a factor of 25.26, 17.92 and 46.83, respectively. Based on the concentration-response curve displacement factors, Compound XII was about 0.7 times as active as cimetidine while BL-5949 was about 1.89 times as active as cimetidine. Thus, BL-5949 was about 2.7 times as active as Compound XII in this test.

into a graduated test tube for volume determination. Titratable acidity is measured by titrating a one ml. sample to pH 7.0 with 0.02 N NaOH, using an Autoburet and an electrometric pH meter (Radiometer). Titratable acid output is calculated in microequivalents by multiplying the volume in milliliters by the acid concentration in milliequivalents per liter. The percent inhibition of acid output is calculated as follows:

$$\% \text{ Inhibition Acid Output} = \frac{\text{Acid Output-Control} - \text{Acid Output-Drug}}{\text{Acid Output-Control}}$$

The results obtained with BL-5949, Compound XII and cimetidine are presented in Table 2. These results indicate that, in the two hour pylorus ligated rat preparation, BL-5949 is 2.26 and Compound XII 0.61 times as potent as cimetidine with respect to the inhibition of gastric acid output. It is also evident that BL-5949 is 3.7 times more potent than Compound XII in this test.

Table 1

Relative Activity of Cimetidine, Compound XII and BL-5949 in Isolated Guinea Pig Right Atria

| Compound | N | Concentration | Histamine ED50 With 95% Confidence Limits (μg/ml) | Concentration-Response Curve Displacement Factor | Activity Ratio Relative to Cimetidine |
|---|---|---|---|---|---|
| Histamine control | 8 | — | 0.19 (0.15–0.24) | — | — |
| Cimetidine | 8 | $3 \times 10^{-5}$M | 4.80 (3.9–5.9) | 25.26 | 1.0 |
| Histamine control | 2 | — | 0.24 (0.16–0.36) | — | — |
| Compound XII | 2 | $3 \times 10^{-5}$M | 4.30 (3.10–5.98) | 17.92 | 0.70 |
| Histamine control | 5 | — | 0.30 (0.24–0.36) | — | — |
| BL-5949 | 5 | $3 \times 10^{-5}$M | 14.05 (12.50–15.90) | 46.83 | 1.89 |

N = number of experiments.

Determination of Gastric Antisecretory Activity in the Two Hour Pylorus Ligated (Shay) Rat The pyloric ligation procedure in the rat was designed by Shay et al., Gastroenterology, 5, 53 (1945) for the study of perforating gastric ulcers; however, as the method became known, it was also employed as a means of studying rat gastric secretion, Shay et al., Gastroenterology, 26, 906 (1954), Brodie, D. A., Am. J. Dig. Dis., 11, 231 (1966). A modification of this procedure is presently used to evaluate compounds for gastric antisecretory activity.

Male Long Evans rats, 280–300 gm., are used. The animals are placed in individual cages and fasted for 24 hours with free access to water. Under ether anesthesia, the stomach is reached through a midline incision, and a cotton-thread ligature is placed around the pylorus. After wound closure, ether administration is stopped and either BL-5949, Compound XII, cimetidine or vehicle is administered intraperitoneally in a volume of 1 mg./kg. All compounds are solubilized with one equivalent of HCl and brought to the proper volume with water. The animals are returned to their cages from which the water bottles have been removed and two hours later are sacrificed with ether. The stomach is removed and the two hour gastric collection is drained Table 2

Effect of BL-5949, Compound XII and Cimetidine on Gastric Acid Output in the Two Hour Pylorus Ligated Rat

| Compound | Dose (ip)[a] μMole/kg | Percent Inhibition Acid Output | ED50 μMole/kg | Potency Ratio |
|---|---|---|---|---|
| BL-5949 | 20 | 87 | | |
| | 5 | 51 | 4.62 | 2.26 |
| | 2.5 | 33 | | |
| Compound XII | 40 | 86 | | |
| | 20 | 64 | 17.2 | 0.61 |
| | 10 | 25 | | |
| Cimetidine | 40 | 72 | | |
| | 20 | 57 | | |
| | 10 | 41 | 10.4 | 1.00 |
| | 5 | 53 | | |
| | 2.5 | 9 | | |

[a]Five to 10 animals were employed at each dose

Determination of Gastric Antisecretory Activity in the Gastric Fistula Dog

Thomas type [Thomas, J. E., Proc. Soc. exp. Biol. Med., 46, 260 (1941)] stainless steel cannulae are inserted into the stomachs of beagle dogs (10–12 kg.) just orad to the pyloric gland area near the greater curvature to provide a chronic gastric fistula. Animals are allowed to recover for at least two months before any testing is done. Dogs are fasted overnight (~18 hours) with water ad lib prior to each experiment. The dogs are placed in a sling and an eight inch inside needle catheter (C. R. Baird, Inc.) with a two inch 17 gauge needle is inserted into a leg vein for purposes of drug administration. Gastric secretions are collected every 15 minutes by gravity drainage from the opened cannula. Basal secretions are collected for two consecutive 15 minute periods and if these prove to be excessive (>4 ml./15 min.; pH<5.0) the animal is not used. A modification of the procedure described by Grossman and Konturek, Gastroenterology, 66, 517 (1974) was followed: Immediately after the second basal collection, histamine (100 μg./kg./hr.) is infused for 90 minutes with a Harvard Infusion Pump in a volume of 6 ml./hr. At this time either BL-5949, Compound XII, cimetidine (solubilized with one equivalent of HCl and brought a proper volume with normal saline) or normal saline is injected rapidly (within 30 seconds) in a volume of 0.1 ml./kg. and then infusion of hisatamine continues for an additional 60 minutes (total time of infusion is 2.5 hours). Each 15 minute sample of gastric juice is measured to the nearest 0.5 ml. and titratable acidity against 0.02 N NaOH (endpoint pH 7.0) is measured with an Autoburet and pH meter (radiometer). The percent inhibition of acid output is calculated as described in the pylorus ligated rat procedure.

BL-5949, Compound XII and cimetidine were administered to the dogs and the results obtained are presented in Table 3. These results indicate that as an inhibitor of histamine-induced gastric acid output in the dog, BL-5949 is 5.56 and Compound XII is 1.47 times more potent than cimetidine. It is also evident that BL-5949 is 3.8 times more potent than Compound XII.

Table 3

Effect of BL-5949, Compound XII and Cimetidine on Gastric Acid Output in the Gastric Fistula Dog

| Compound | Dose (iv)[a] μMole/kg | Percent Inhibition Acid Output | ED50 μMole/kg | Potency Ratio |
|---|---|---|---|---|
| BL-5949 | 1.50[b] | 88 | | |
| | 0.75 | 68 | | |
| | 0.375 | 62 | 0.24 | 5.56 |
| | 0.1875 | 46 | | |
| | 0.0938 | 34 | | |
| Compound XII | 1.50 | 73 | | |
| | 0.75 | 42 | 0.90 | 1.47 |
| | 0.375 | 22 | | |
| Cimetidine | 3.0 | 73 | | |
| | 1.5 | 53 | 1.33 | 1.00 |
| | 0.75 | 37 | | |

[a] Three to 11 dogs were employed at each dose
[b] One dog at this dose

EXAMPLE 1

1-Nitro-2-(2-propynylamino)-2-{2-[(4-methyl-1H-imidazol-5-yl)methylthio]ethylamino}ethylene (BL-5949)

A mixture of 1-nitro-2-methylthio-2-{2-[(4-methyl-1H-imidazol-5-yl)methylthio]ethylamino}ethylene prepared according to Belgian Pat. No. 814,941 (4.0 g, 0.014 mole) and distilled propargylamine (7.74 g, 0.14 mole) in acetonitrile (60 ml) was stirred at reflux temperature under a positive pressure of nitrogen for 18 hours. The reaction mixture was cooled, evaporated to dryness and then triturated under 20 ml of isopropyl alcohol to give the title compound (3.58 g, 87%). Column chromatography on silica gel by gradient elution using methylene chloride-methanol gave a pure sample; mp 159°-160° dec.

Anal. Calcd for $C_{12}H_{17}N_5O_2S$: C, 48.80; H, 5.80; N, 23.71; S, 10.86. Found: C, 48.53; H, 5.76; N, 24.10; S, 10.87.

EXAMPLE 2

1-Nitro-2-(2-butyn-1-ylamino)-2-{2-[(4-methyl-1H-imidazol-5-yl)methylthio]ethylamino}ethylene (BL-5979)

A mixture of 1-nitro-2-methylthio-2-{2-[(4-methyl-1H-imidazol-5-yl)methylthio]ethylamino}ethylene (2.25 g, 7.8 mmole) and 2-butyn-1-amine (2.16 g, 31.2 mmole) in acetonitrile (35 ml) was stirred under a positive pressure of nitrogen at reflux temperature for 7 hours and at room temperature for 15 hours. The solvent was removed by evaporation under reduced pressure, and the residue placed on silica gel and chromatographed by gradient elution using methylene chloride-methanol. The appropriate fractions yielded 1.93 g (80%) of the title product from acetonitrile. Recrystallization from isopropyl alcohol gave the product with mp 147.5°-151°.

Anal. Calcd for $C_{13}H_{19}N_5O_2S$: C, 50.47; H, 6.19; N, 22.64; S, 10.36. Found: C, 50.51; H, 6.26; N, 22.64; S, 10.21.

EXAMPLE 3

1-Nitro-2-(4-pentyn-1-amino)-2-{2-[(4-methyl-1H-imidazol-5-yl) methylthio]ethylamino}ethylene (BL-5978)

A mixture of 1-nitro-2-methylthio-2-{2-[(4-methyl-1H-imidazol-5-yl)methylthio]ethylamino}ethylene (2.12 g, 7.34 mmole) and 4pentyn-1-amine (2.44 g, 29.4 mmole) in acetonitrile (30 ml) was stirred at reflux temperature under a positive pressure of nitrogen for 4 hours. The reaction mixture was evaporated under reduced pressure and the residue was placed on silica gel and chromatographed by gradient elution using methylene chloride-methanol. The appropriate fractions were combined and the product recrystallized from acetonitrile to give the title compound; mp 105°-108°.

Anal. Calc for $C_{14}H_{21}N_5O_2S$: C, 51.99; H, 6.54; N, 21.65; S, 9.91. Found: C, 51,87; H, 6.51; N, 21.97; S, 9.98.

EXAMPLE 4

1-Nitro-2-(3-butyn-2-ylamino)-2-{2-[(4-methyl-1H-imidazol-5-yl)methylthio]ethylamino}ethylene A mixture of 1-nitro-2-methylthio-2-{2-[(4-methyl-1H-imidazol-5-yl)methylthio]ethylamino}ethylene (3.13 g, 10.9 mmole) and 3-amino-1-butyne (4.5 g, 65.1 mmole) in acetonitrile (45 ml) was stirred at reflux temperature under a positive pressure of nitrogen for 17 hours. The reaction mixture was evaporated under reduced pressure then the residue placed on silica gel and chromatographed by gradient elution using methylene chloride-methanol. Recrystallization yielded the title compound.

EXAMPLE 5

1,1-Dicyano-2-(2-propynylamino)-2-{2-[(4-methyl-1H-imidazol-5-yl)methylthio]ethylamino}ethylene (BL-5965)

A.

1,1-Dicyano-2-methylthio-2-{2-[(4-methyl-1H-imidazol-5-yl)methylthio]ethylamino}ethylene Bis(methylthio)methylenemalononitrile [prepared according to the procedure described in *Chem. Ber.*, 95, 2861 (1962)] (9.94 g, 58.4 mmole) was added with stirring to a solution of 2-[(4-methyl-1H-imidazol-5-yl)methylthio]ethylamine (10.0 g, 58.4 mmole) in 100 ml of absolute ethanol. After stirring at room temperature for 90 minutes, the solvent was removed by evaporation under reduced pressure, and the residue placed on silica gel and chromatographed to yield the title compound (15.65 g).

B.

1,1-Dicyano-2-(2-propynylamino)-2-{2-[(4-methyl-1H-imidazol-5-yl)methylthio]ethylamino}ethylene (BL-5965)

A mixture of the product of Step A (4.3 g, 14.7 mmole) and propargylamine (8.6 ml) in acetonitrile (43 ml) was stirred at reflux temperature under a positive pressure of nitrogen for 15 hours then at room temperature for an additional 48 hours. The reaction mixture was filtered to remove by-product and the filtrate was evaporated under reduced pressure. The residual gum was placed on silica gel and chromatographed by gradient elution using methylene chloride-methanol. The appropriate fractions were combined and the product recrystallized from acetonitrile to give the title compound; mp 112.5°-115°.

Anal. Calcd for $C_{14}H_{16}N_6S$: C, 55.98; H, 5.37; N, 27.98; S, 10.67. Found: C, 55.89; H, 5.46; N, 27.95; S, 10.70.

EXAMPLE 6

1-Carbamoyl-1-cyano-2-(2-propynylamino)-2-{2-[(4-methyl-1H-imidazol-5-yl)methylthio]ethylamino}ethylene (BL-5977)

A.

1-Carbamoyl-1-cyano-2-methylthio-2-{2-[(4-methyl-1H-imidazol-5-yl)methylthio]ethylamino}ethylene (BL-5986)

To a solution of 2-[(4-methyl-1H-imidazol-5-yl)methylthio]ethylamine (10.0 g, 58.4 mmole) in 100 ml of absolute ethanol was added with stirring 2,2-bis(methylthio)-1-cyanoacrylamide [prepared according to the procedure described in *Chem. Ber.*, 95, 2861 (1962)] (10.99 g, 58.4 mmole). Stirring was continued at room temperature for 16 hours, then the solvent was removed at reduced pressure. The residue was placed on silica gel and chromatographed by gradient elution using methylene chloride-methanol to give the product. Recrystallization from acetonitrile gave the title compound; mp 137°-139°.

Anal Calcd for $C_{12}H_{17}N_5OS_2$: C, 46.28; H, 5.50; N, 22.49; S, 20.59. Found: C, 46.35; H, 5.58; N, 22.60; S, 20.03.

B.

1-Carbamoyl-1-cyano-2-(2-propynylamino)-2-{2-[(4-methyl-1H-imidazol-5-yl)methylthio]ethylamino}ethylene (BL-5977)

A mixture of the product of Step A (4.0 g, 12.8 mmole) and propargylamine (8.0 ml) in acetonitrile (40 ml) was stirred at reflux temperature under a positive pressure of nitrogen for 16 hours. The reaction mixture was cooled and evaporated to dryness under reduced pressure, and the residue was placed on silica gel and chromatographed by gradient elution using methylene chloride-methanol. Recrystallization from acetonitrile gave the title compound; mp 88°-94° (partial melt at 66°-69°).

Anal. Calcd for $C_{14}H_{18}N_6OS \cdot CH_3CN$: C, 53.46; H, 5.89; N, 27.28; S, 8.92. Found: C, 53.18; H, 5.92; N, 27.17; S, 8.94.

EXAMPLE 7

1-Nitro-2-(3-butyn-1-ylamino)-2-{2-[(4-methyl-1H-imidazol-5-yl)methylthio]ethylamino}ethylene The general procedure of Example 2 is repeated except that the 2-butyn-1-amine utilized therein is replaced by an equimolar amount of 3-butyn-1-amine [prepared by the procedure described in *Bull. Soc. Chim. Fr.*, 588 (1967)], and the title product is produced.

EXAMPLE 8

1-Nitro-2-(2-methyl-3-butyn-2-ylamino)-2-{2-[(4-methyl-1H-imidazol-5-yl)methylthio]ethylamino}ethylene The general procedure of Example 2 is repeated except that the 2-butyn-1-amine utilized therein is replaced by an equimolar amount of 1,1-dimethylpropargylamine, and the title product is produced.

EXAMPLE 9

1-Benzenesulfonyl-1-cyano-2-(2-propynylamino)-2-{2-[(4-methyl-1H-imidazol-5-yl)methylthio]ethylamino}ethylene

A.

1-Benzenesulfonyl-1-cyano-2-methylthio-2-{2-[(4-methyl-1H-imidazol-5-yl)methylthio]ethylamino}ethylene Equimolar amounts of 1-benzenesulfonyl-1-cyano-2,2-bis(methylthio)ethylene [prepared according to the procedure described by M. Augustin et al., *Z. Chem.*, 17, 289 (1977)] and 2-[(4-methyl-1H-imidazol-5-yl)methylthio]ethylamine [prepared according to the procedure described in U.S. Pat. No. 3,950,353] are reacted according to the general procedure of Example 6A, and the title product is produced.

B.

1-Benzenesulfonyl-1-cyano-2-(2-propynylamino)-2-{2-[(4-methyl-1H-imidazol-5-yl)methylthio]ethylamino}ethylene The product of Step A is reacted with a four-fold excess of propargylamine according to the general procedure of Example 2, and the title product is produced.

EXAMPLE 10

The literature procedure for preparing 1-benzenesulfonyl-1-cyano-2,2-bis(methylthio)ethylene [*Z. Chem.*, 17, 289 (1977)] is repeated except that the phenylsulfonylacetonitrile utilized therein is replaced by an equimolar amount of
(4-chlorophenyl)sulfonylacetonitrile,
(3,4-dichlorophenyl)sulfonylacetonitrile,
(4-methylphenyl)sulfonylacetonitrile,
bis(phenylsulfonyl)methane and
phenylsulfonylnitriomethane, respectively,
and there is thereby produced
1-(4-chlorophenyl)sulfonyl-1-cyano-2,2-bis(methylthio)ethylene,
1-(3,4-dichlorophenyl)sulfonyl-1-cyano-2,2-bis(methylthio)ethylene,
1-(4-methylphenyl)sulfonyl-1-cyano-2,2-bis(methylthio)ethylene,
1,1-bis(phenylsulfonyl)-2,2-bis(methylthio)ethylene and
1-benzenesulfonyl-1-nitro-2,2-bis(methylthio)ethylene, respectively.

Each of the above products are individually reacted with 2-[(4-methyl-1H-imidazol-5-yl)methylthio]ethylamine according to the general procedure of Example 9, Step A, and the resulting intermediates are individually reacted with propargylamine according to the general procedure of Example 9, Step B, and there is thereby produced
1-(4-chlorophenyl)sulfonyl-1-cyano-2-(2-propynylamino)-2-{2-[(4-methyl-1H-imidazol-5-yl)methylthio]ethylamino}ethylene,
1-(3,4-dichlorophenyl)sulfonyl-1-cyano-2-(2-propynylamino)-2-{2-[(4-methyl-1H-imidazol-5-yl)methylthio]ethylamino}ethylene,
1-(4-methylphenyl)sulfonyl-1-cyano-2-(2-propynylamino)-2-{2-[(4-methyl-1H-imidazol-5-yl)methylthio]ethylamino}ethylene,
1,1 bis(phenylsulfonyl)-2-(2-propynylamino)-2-{2-[(4-methyl-1H-imidazol-5-yl)methylthio]ethylamino}ethylene and
1-benzenesulfonyl-1-nitro-2-(2-propynylamino)-2-{2-[(4-methyl-1H-imidazol-5-yl)methylthio]ethylamino}ethylene, respectively.

EXAMPLE 11

1-Nitro-2-(2-propynylamino)-2-{2-[(4-bromo-1H-imidazol-5-yl)methylthio]ethylamino}ethylene When 2-[(4-bromo-1H-imidazol-5-yl)methylthio]ethylamine (prepared according to the procedure described in Belgian Pat. No. 779,775]) is reacted with 1,1-bis(methylthio)-2-nitroethylene according to the procedure of Example 6, Step A, and the resultant 1-nitro-2-methylthio-2-{2-[(4-bromo-1H-imidazol-5-y;)methylthio]ethylamino}ethylene is treated with propargylamine by the procedure of Example 6, Step B, the title compound is produced.

EXAMPLE 12

1-Nitro-2-(2-propynylamino)-2-{2-[(4-hydroxymethyl-1H-imidazol-5-yl)methylthio]ethylamio}ethylene When 2-[(4-hydroxymethyl-1H-imidazol-5-yl)methylthio]ethylamine [prepared according to the procedure described in Belgian Pat. No. 843,840] is reacted with 1,1-bis(methylthio)-2-nitroethylene according to the procedure of Example 6, Step A, and the resultant 1-nitro-2-methylthio-2-{2-[(4-hydroxymethyl-1H-imidazol-5-yl)methylthio]ethylamino}ethylene is treated with propargylamine by the procedure of Example 6, Step B, the title compound is produced.

EXAMPLE 13

1-Cyano-2-(2-propynylamino)-2-{2-[(4-methyl-1H-imidazol-5-yl)methylthio]ethylamino}ethylene (a) When 2-[(4-methyl-1H-imidazol-5-yl)methylthio]ethylamine [prepared according to the procedure described in U.S. Pat. No. 3,950,353] is reacted with 1-cyano-2-ethoxy-2-propynylaminoethylene [prepared by the reaction of propargylamine with 1-cyano-2,2-bis(methoxy)ethylene, itself prepared by the procedure described in J. Am. Chem. Soc., 71, 47 (1949)], the title product is produced.

(b) When 2-[(4-methyl-1H-imidazol-5-yl)methylthio]ethylamine is reacted with 1-cyano-2,2-bis(methoxy)ethylene according to the procedure of Example 6, Step A, and the resultant 1-cyano-2-methoxy-2-{2-[(4-methyl-1H-imidazol-5-yl)methylthio]ethylamino}ethylene is treated with propargylamine by the procedure of Example 6, Step B, the title compound is produced.

EXAMPLE 14

1-Benzenesulfonyl-2-(2-propynylamino)-2-{2-[(4-methyl-1H-imidazol-5-yl)methylthio]ethylamino}ethylene Reaction of methylphenylsulfone with carbon disulphide under strongly basic conditions and treatment of the product with methyl iodide yields 1-benzenesulphonyl-2,2-bis(methylthio)ethylene. When 1-benzenesulfonyl-2,2-bis(methylthio)ethylene is reacted with 2-[(4-methyl-1H-imidazol-5-yl)methylthio]ethylamine according to the procedure of Example 6, Step A, the product is 1-benzenesulfonyl-2-methylthio-2-{2-[(4-methyl-1H-imidazol-5-yl)methylthio]ethylamino}ethylene. Reaction of this methylthio compound with propargylamine by the procedure of Example 6, Step B, yields the title compound.

EXAMPLE 15

The general procedure of Example 14 is repeated except that the methylphenylsulfone utilized therein is replaced by an equimolar amount of
methyl-(4-chlorophenyl)sulfone,
methyl-(3,4-dichlorophenyl)sulfone and
methyl-(4-methylphenyl)sulfone, respectively, and there is thereby produced
1-(4-chlorophenyl)sulfonyl-2-(2-propynylamino)-2-{2-[(4-methyl-1H-imidazol-5-yl)methylthio]ethylamino}ethylene,
1-(3,4-dichlorophenyl)sulfonyl-2-(2-propynylamino)-2-{2-[(4-methyl-1H-imidazol-5-yl)methylthio]ethylamino}ethylene and
1-(4-methylphenyl)sulfonyl-2-(2;-propynylamino)-2-{2-[(4-methyl-1H-imidazol-5-yl)methylthio]ethylamino}ethylene, respectively.

EXAMPLE 16

1-Nitro-2-(2-propynylamino)-2-{2-[(4-methyl-1H-imidazol-5-yl)methylthio]propylamino}ethylene When 3-[(4-methyl-1H-imidazol-5-yl)methylthio]propylamine [prepared according to the procedure described in Belgian Pat. No. 804,144] is reacted with 1,1-bis(methylthio)-2-nitroethylene according to the procedure of Example 6, Step A, and the resultant 1-nitro-2-methylthio-2-{3-[(4-methyl-1H-imidazol-5-yl)methylthio]propylamino}ethylene is treated with propargylamine by the procedure of Example 6, Step B, the title compound is produced.

EXAMPLE 17

When 1,1-bis(methylthio)-2-carbomethoxy-2-cyanoethylene [prepared according to the procedure described in Chem. Ber., 95, 2861 (1962)] is reacted with 2-[(4-methyl-1H-imidazol-5-yl)methylthio]ethylamine according to the procedure of Example 6, Step A, and the resultant 1-carbomethoxy-1-cyano-2-methylthio-2-{2-[(4-methyl-1H-imidazol-5-yl)methylthio]ethylamino}ethylene treated with propargylamine by the procedure of Example 6, Step B, there is produced 1-carbomethoxy-1-cyano-2-(2-propynylamino)-2-{2-[(4-methyl-1H-imidazol-5-yl)methylthio]ethylamino}ethylene.

When the above procedure is repeated, except that the 1,1-bis(methylthio)-2-carboxymethyl-2-cyanoethylene utilized therein is replaced by
1,1-bis(methylthio)-2-benzoyl-2-cyanoethylene,
1,1-bis(methylthio)-2-benzoyl-2-ethoxycarbonylethylene,
1,1-bis(methylthio)-2-acetyl-2-benzoylethylene and
1,1-bis(methylthio)-2-(N-methylcarbamoyl)-2-cyanoethylene, respectively, [each prepared by the procedure described in Acta Chem. Scand., 24, 1191 (1970) or Chem. Ber., 95, 2861 (1962)] there is obtained
1-benzoyl-1-cyano-2-(2-propynylamino)-2-{2-[(4-methyl-1H-imidazol-5-yl)methylthio]ethylamino}ethylene,
1-benzoyl-1-ethoxycarbonyl-2-(2-propynylamino)-2-{2-[(4-methyl-1H-imidazol-5-yl)methylthio]ethylamino}ethylene,
1-acetyl-1-benzoyl-2-(2-propynylamino)-2-{2-[(4-methyl-1H-imidazol-5-yl)methylthio]ethylamino}ethylene and
1-cyano-1-(N-methylcarbamoyl)-2-(2-propynylamino)-2-{2-[(4-methyl-1H-5-yl)methylthio]ethylamino}ethylene, respectively.

EXAMPLE 18

1-Nitro-2-(propynylamino)-2-{2-[(4-methyl-1H-imidazol-5-yl)methylthio]ethylamino}ethylene BL-5949

A. 1-Methylthio-1-(2-propynylamino)-2-nitroethylene

A solution of propargylamine (1.10 g, 0.02 mole) in 22 ml of methanol was added dropwise to a stirred suspension of 1-methylsulfinyl-1-methylthio-2-nitroethylene [prepared according to the procedure described in Belgian Pat. No. 841,353], at 25°. After 1 hour at ambient temperature the solution was evaporated under reduced pressure, triturated under 20 ml of cold isopropanol, and filtered to give the product. Recrystallization from isopropanol gave the title product, mp 131°–132°.

B.
1-Nitro-2-(propynylamino)-2-{2-[(4-methyl-1H-imidazol-5-yl)methylthio]ethylamino}ethylene BL-5949

A solution of the product of Step A is treated with about an equimolar amount of 2-[(4-methyl-1H-imidazol-5-yl)methylthio]ethylamine [prepared by the procedure described in U.S. Pat. No. 3,950,353] to produce, after workup and chromatography, the title product.

EXAMPLE 19

A solution of propargylamine in isopropanol is slowly added to an isopropanol solution containing an approximately equimolar amount of
1,1-bis(methylthio)-2-nitroethylene,
1,1-bis(ethylthio)-2-nitroethylene,
1,1-bis(benzylthio)-2-nitroethylene and
1,1-bis(2,4-dinitrophenylthio)-2-nitroethylene, respectively, and there is thereby produced
1-methylthio-1-(2-propynylamino)-2-nitroethylene,
1-ethylthio-1-(2-propynylamino)-2-nitroethylene,
1-benzylthio-1-(2-propynylamino)-2-nitroethylene and
1-(2,4-dinitrophenylthio)-1-(2-propynylamino)-2-nitroethylene, respectively.

Reaction of each of the above products with 2-[(4-methyl-1H-imidazol-5-yl)methylthio]ethylamine produces 1-nitro-2-(propynylamino)-2-{2-[(4-methyl-1H-imidazol-5-yl)methylthio]ethylamino}ethylene (BL-5949).

The 1,1-bis(methylthio)-2-nitroethylene, 1,1-bis(ethylthio)-2-nitroethylene and 1,1-bis(benzylthio)-2-nitroethylene starting materials are prepared by procedures described in Chem. Ber., 100, 591 (1967) and Acta Chem. Scand., 21, 2797 (1967). The 1,1-bis(2,4-dinitrophenylthio)-2-nitroethylene starting material is prepared by the reaction of 2,4-dinitrofluorobenzene and dipotassium nitrodithioacetate.

EXAMPLE 20

A solution of cysteamine hydrochloride in dimethylformamide is reacted with about an equimolar amount of
1-methylthio-1-(2-propynylamino)-2-nitroethylene,
1-ethylthio-1-(2-propynylamino)-2-nitroethylene,
1-benzylthio-1-(2-propynylamino)-2-nitroethylene and
1-(2,4-dinitrophenylthio)-1-(2-propynylamino)-2-nitroethylene, respectively, in the presence of about one equivalent of base, and there is produced in each case 1-nitro-2-(2-propynylamino)-2-(2-mercaptoethyl)ethylene.

When the above product is reacted with 4-methyl-5-chloromethylimidazole hydrochloride and one equivalent of base, there is produced 1-nitro-2-(2-propynylamino)-2-{2-[(4-methyl-1H-imidazol-5-yl)methylthio]ethylamino}ethylene (BL-5949).

We claim:
1. A compound of the formula

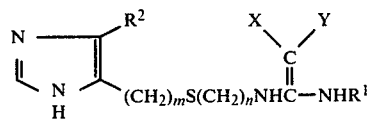

wherein $R^1$ is a straight or branched chain alkynyl group containing from 3 to 9 carbon atoms, inclusive; $R^2$ is hydrogen, (lower)alkyl, halogen, or hydroxymethyl; m is 1 or 2, and n is 2 or 3, provided that the sum of m and n is 3 or 4; X and Y each are independently hydrogen, nitro, cyano, $-SO_2Ar$ or $-COR^3$, provided that X and Y are not both hydrogen; $R^3$ is (lower)alkyl, Ar, (lower)alkoxy, amino or (lower)alkylamino; and Ar is phenyl or phenyl containing 1 or 2 substituents independently selected from halogen and (lower)alkyl; or a nontoxic pharmaceutically acceptable acid addition salt thereof.

2. A compound of claim 1 having the formula

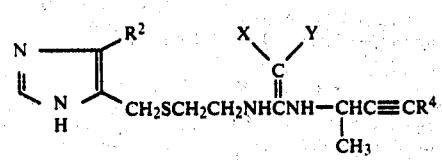

wherein $R^2$, X and Y are as defined in claim 1, and $R^4$ is hydrogen or methyl, or a nontoxic pharmaceutically acceptable acid addition salt thereof.

3. A compound of claim 1 having the formula

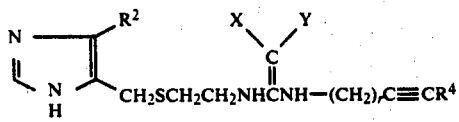

wherein $R^2$, X and Y are as defined in claim 1, $R^4$ is hydrogen or methyl and r is an integer of from 1 to 6, inclusive, or a nontoxic pharmaceutically acceptable acid addition salt thereof.

4. A compound of claim 1 having the formula

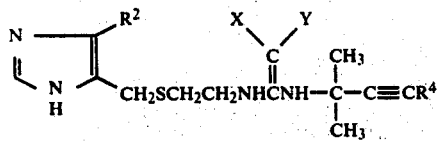

wherein $R^2$, X and Y are as defined in claim 1, and $R^4$ is hydrogen or methyl, or a nontoxic pharmaceutically acceptable acid addition salt thereof.

5. A compound of claim 1 having the formula

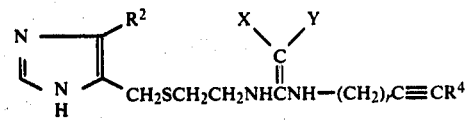

wherein $R^2$ is hydrogen, methyl, chloro, bromo or hydroxymethyl; X and Y are each independently hydrogen, nitro, cyano or carbamoyl, provided that X and Y are not both hydrogen; r is an integer of from 1 to 6; and $R^4$ is hydrogen or methyl; or a nontoxic, pharmaceutically acceptable salt thereof.

6. 1-Carbamoyl-1-cyano-2-(2-propynylamino)-2-{2-[(4-methyl-1H-imidazol-5-yl)methylthio]ethylamino}ethylene or a nontoxic pharmaceutically acceptable salt thereof.

7. 1,1-Dicyano-2-(2-propynylamino)-2-{2-[(4-methyl-1H-imidazol-5-yl)methyltnhio]ethylamino}ethylene or a nontoxic pharmaceutically acceptable salt thereof.

8. 1-Nitro-2-(2-methyl-3-butyn-2-ylamino)-2-{2-[(4-methyl-1H-imidazol-5-yl)methylthio]ethylamino}ethylene or a nontoxic pharmaceutically acceptable salt thereof.

9. 1-Nitro-2-(3-butyn-1-ylamino)-2-{2-[(4-methyl-1H-imidazol-5-yl)methylthio]ethylamino}ethylene or a nontoxic pharmaceutically acceptable salt thereof.

10. 1-Nitro-2-(3-butyn-2-ylamino)-2-{2-[(4-methyl-1H-imidazol-5-yl)methylthio]ethylamino}ethylene or a nontoxic pharmaceutically acceptable salt thereof.

11. 1-Nitro-3-(4-pentyn-1-ylamino)-2-{2-[(4-methyl-1H-imidazol-5-yl)methylthio]ethylamino}ethylene or a nontoxic pharmaceutically acceptable salt thereof.

12. 1-Nitro-2-(2-butyn-1-ylamino)-2-{2-[(4-methyl-1H-imidazol-5-yl)methylthio]ethylamino}ethylene or a nonotoxic pharmaceutically acceptable salt thereof.

13. 1-Nitro-2-(2-propynylamino)-2-{2-[(4-methyl-1H-imidazol-5-yl)methylthio]ethylamino}ethylene.

14. A nontoxic, pharmaceutically acceptable salt of the compound of claim 13.

* * * * *

UNITED STATES PATENT AND TRADEMARK OFFICE
CERTIFICATE OF CORRECTION

PATENT NO. : 4,200,760
DATED : April 29, 1980
INVENTOR(S) : Aldo A. Algieri et al.

It is certified that error appears in the above-identified patent and that said Letters Patent are hereby corrected as shown below:

In Claim 7, Line 2 thereof, "methyltnhio" should read -- methylthio --.

In Claim 11, Line 1 thereof, "1-Nitro-3-" should read -- 1-Nitro-2- --.

In Column 22, Line 53, "(2;-propynylamino)" should read -- (2-propynylamino) --.

Signed and Sealed this

First Day of July 1980

[SEAL]

Attest:

SIDNEY A. DIAMOND

Attesting Officer

Commissioner of Patents and Trademarks